US012121693B2

(12) United States Patent
Thorne et al.

(10) Patent No.: US 12,121,693 B2
(45) Date of Patent: Oct. 22, 2024

(54) LIMITED STEP METHODS AND APPARATUS FOR MEDICINE STERILIZING AND BOTTLING

(71) Applicant: Thorne Intellectual Property Holdings, LLC, Bountiful, UT (US)

(72) Inventors: Gale Harrison Thorne, Bountiful, UT (US); Gale Harrison Thorne, Jr., Bountiful, UT (US)

(73) Assignee: THORNE INTELLECTUAL PROPERTY HOLDINGS, LLC, Bountiful, UT (US)

( * ) Notice: Subject to any disclaimer, the term of this patent is extended or adjusted under 35 U.S.C. 154(b) by 221 days.

(21) Appl. No.: 17/803,379

(22) Filed: Jun. 6, 2022

(65) Prior Publication Data

US 2023/0181815 A1    Jun. 15, 2023

Related U.S. Application Data

(63) Continuation-in-part of application No. 17/300,842, filed on Dec. 13, 2021.

(51) Int. Cl.
| | |
|---|---|
| *B65B 3/00* | (2006.01) |
| *A61F 9/00* | (2006.01) |
| *A61M 5/00* | (2006.01) |
| *A61M 5/315* | (2006.01) |
| *A61M 5/14* | (2006.01) |

(52) U.S. Cl.
CPC ........... *A61M 5/002* (2013.01); *A61F 9/0026* (2013.01); *A61M 5/31513* (2013.01); *B65B 3/003* (2013.01); *A61M 2005/1402* (2013.01); *A61M 2005/1403* (2013.01)

(58) Field of Classification Search
CPC ......... B65B 3/003; B65B 55/00; B65B 55/02; A61J 1/20; A61J 1/2096
See application file for complete search history.

(56) References Cited

U.S. PATENT DOCUMENTS

| | | | |
|---|---|---|---|
| 5,707,173 A * | 1/1998 | Cottone ................. | A61B 50/36 588/259 |
| 6,164,044 A * | 12/2000 | Porfano ................ | A61M 5/344 53/489 |

(Continued)

OTHER PUBLICATIONS

Jessica Baseggio et al.; Nov. 1, 2021; "Considering A Coating Technology As An Alternative To Silicone Oil" (9 pgs).*

*Primary Examiner* — Gloria R Weeks
(74) *Attorney, Agent, or Firm* — Gale H. Thorne

(57) ABSTRACT

Methods and apparatus for sterilizing and filling vessels which are kept in a sterile environment while being filled are capped before filling and immediately thereafter are ready to be displaced into a potentially contaminating environment while retaining a predetermined SAL are disclosed. Such vessels can be syringes use for dispensing Avastin or conventional syringes. Also method and apparatus for making an eye drop bottle using a conventional medical syringe which can be used in kits made according to the present invention are disclosed. In addition, a method for modifying conventional eye drop bottles for use in kits made according to the instant invention is disclosed. Further, a method for linking single convenience kits to form increased numbers of vessels filled by the same single act, used to fill a single convenience kit, is also disclosed.

13 Claims, 9 Drawing Sheets

(56) References Cited

U.S. PATENT DOCUMENTS

| | | | | |
|---|---|---|---|---|
| 6,331,174 B1* | 12/2001 | Reinhard | ............... | B65B 55/02 |
| | | | | 604/199 |
| 8,449,521 B2* | 5/2013 | Thorne, Jr. | ............... | A61J 1/16 |
| | | | | 604/407 |
| 9,139,316 B2* | 9/2015 | Husnu | ................... | A61J 1/2006 |
| 9,456,956 B1* | 10/2016 | Webster | ................. | A61L 2/081 |
| 9,649,428 B2* | 5/2017 | Timm | ................. | A61K 31/407 |
| 10,226,401 B2* | 3/2019 | Husnu | ................. | A61J 1/2006 |
| 10,440,989 B2* | 10/2019 | Gardella | ................ | B65B 39/12 |
| 10,471,212 B2* | 11/2019 | Ashmead | .......... | A61M 5/31513 |
| 10,555,872 B1* | 2/2020 | Thorne | ................ | A61J 1/2096 |
| 10,800,556 B2* | 10/2020 | Thorne | ................... | A61J 1/05 |
| 11,419,985 B2* | 8/2022 | Wei | .................... | A61M 5/2033 |
| 2011/0094619 A1* | 4/2011 | Steel | ...................... | B65B 55/02 |
| | | | | 24/457 |
| 2013/0220484 A1* | 8/2013 | De Marco | ............ | A61J 1/2037 |
| | | | | 141/183 |
| 2014/0238542 A1* | 8/2014 | Kvale | ................... | B65B 3/003 |
| | | | | 141/329 |
| 2014/0263147 A1* | 9/2014 | Py | ........................ | A61J 1/2096 |
| | | | | 141/2 |
| 2018/0126066 A1* | 5/2018 | Narvekar | ............... | B65B 55/20 |
| 2018/0325728 A1* | 11/2018 | Weikart | ................. | A61P 27/02 |
| 2021/0283015 A1* | 9/2021 | Troschl | .................. | B65B 3/003 |

* cited by examiner

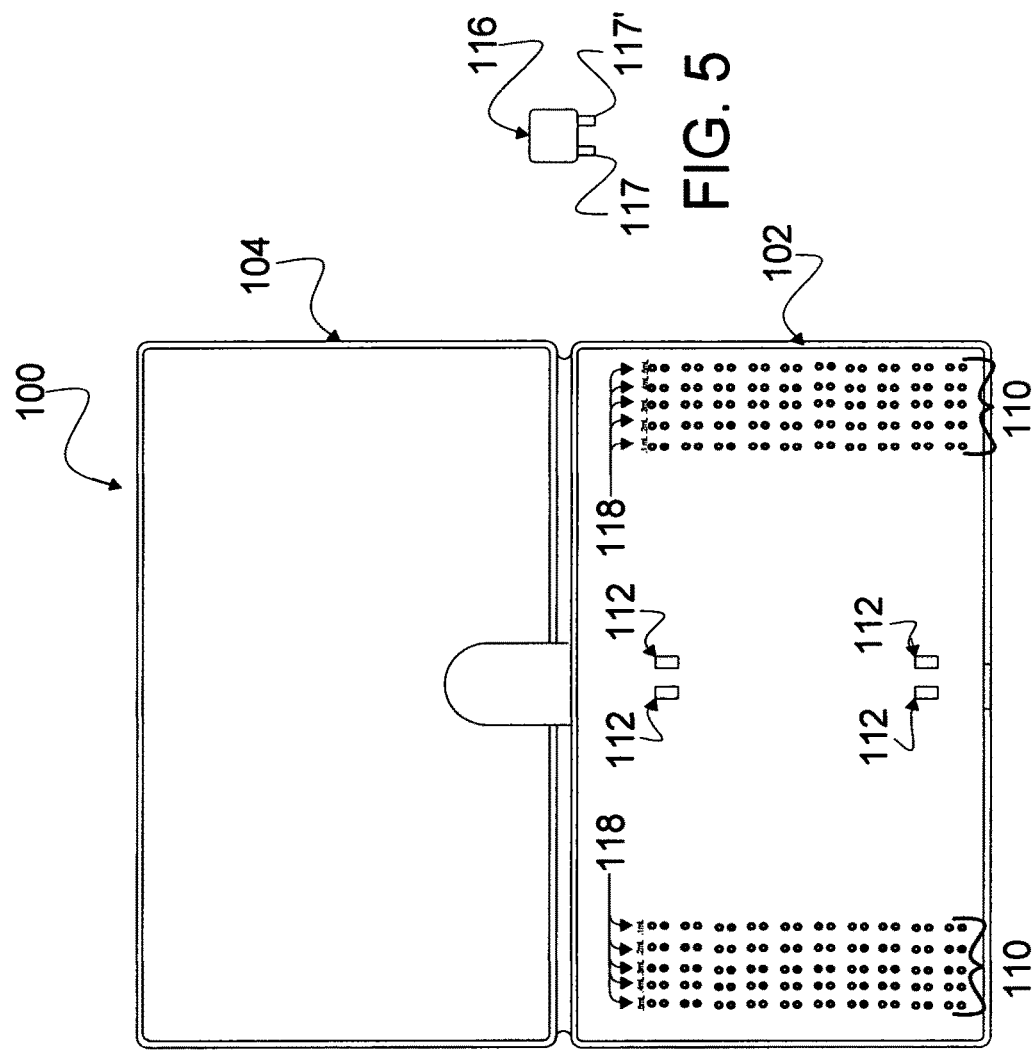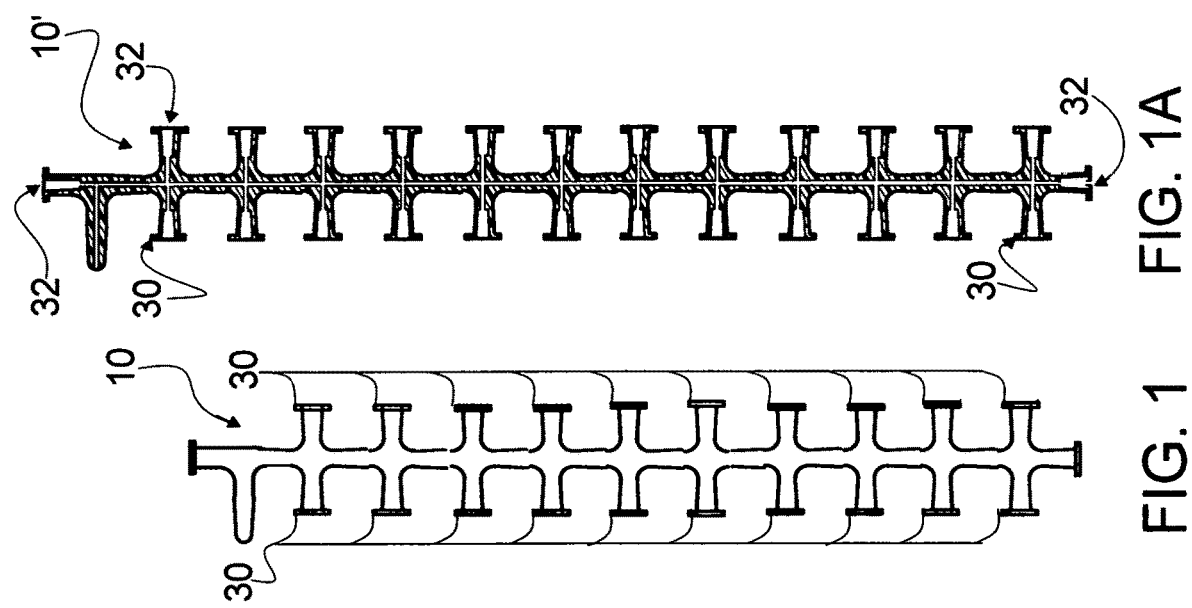

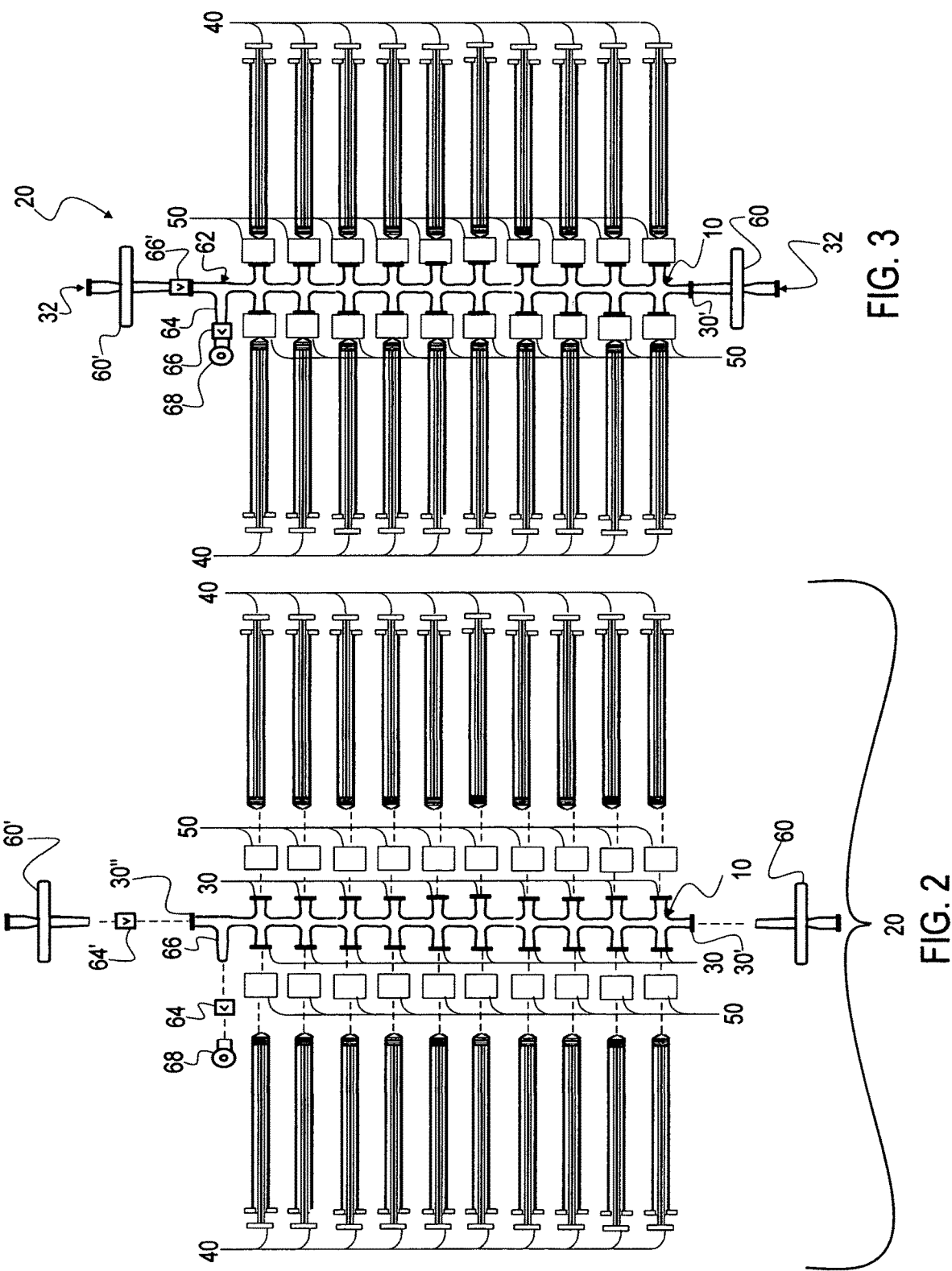

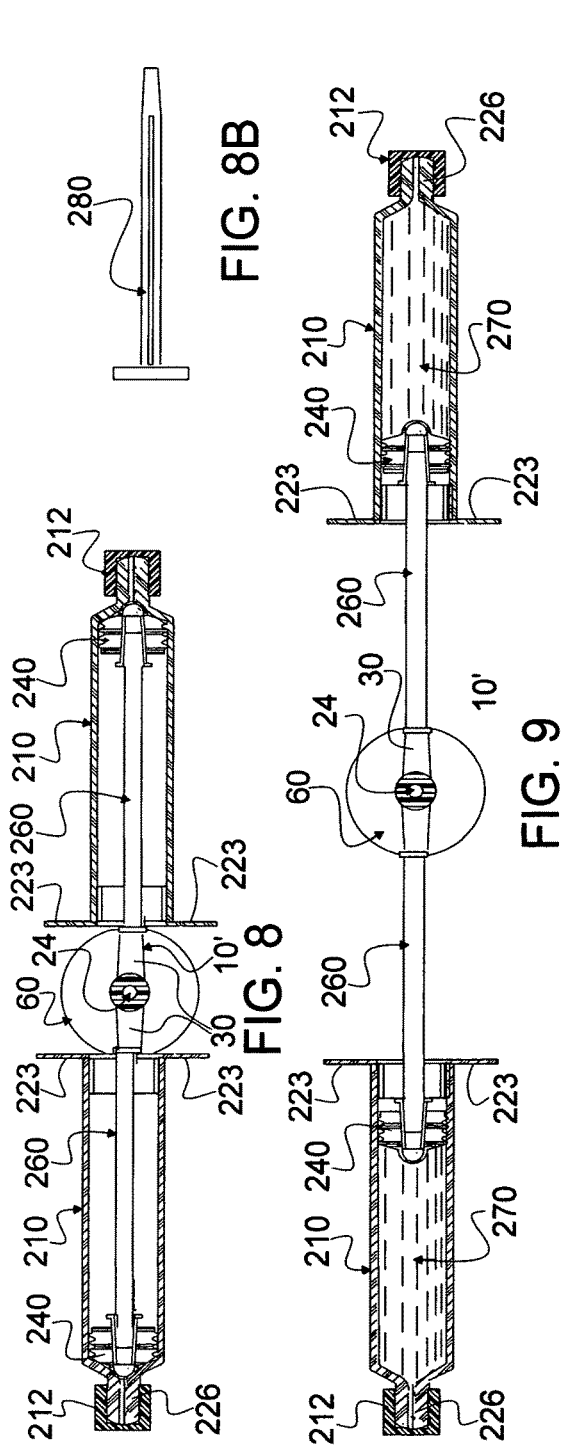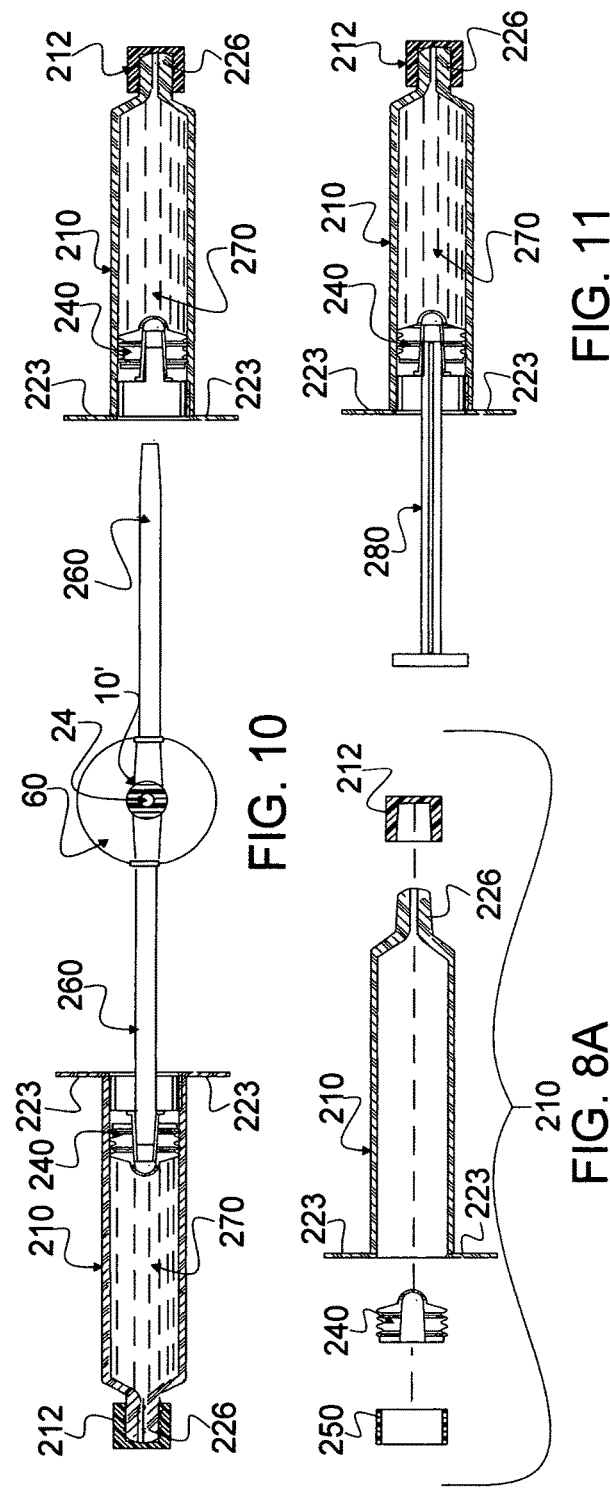

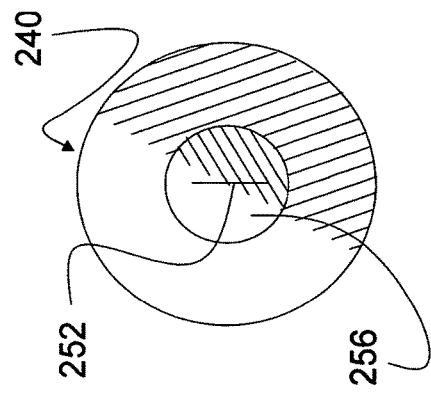
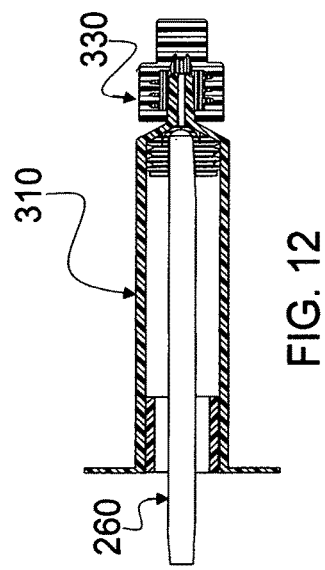
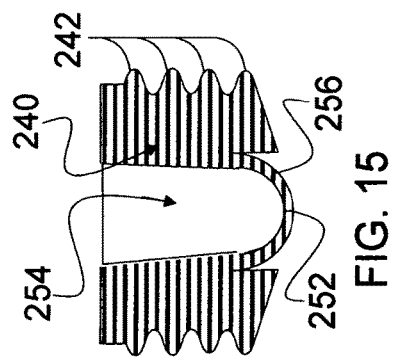
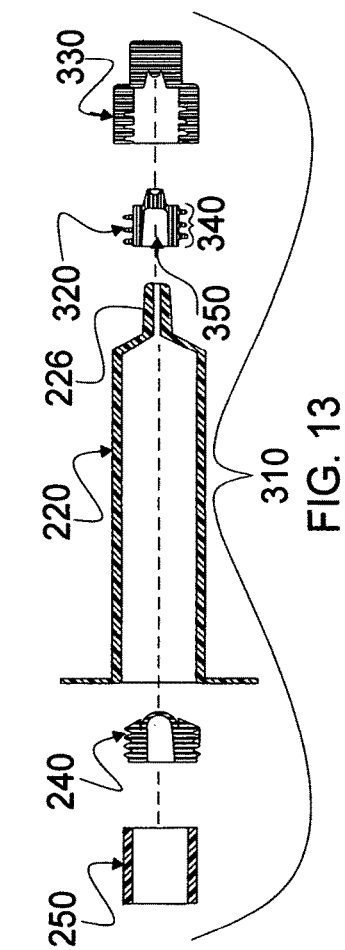
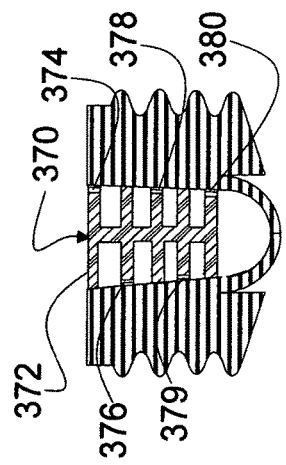
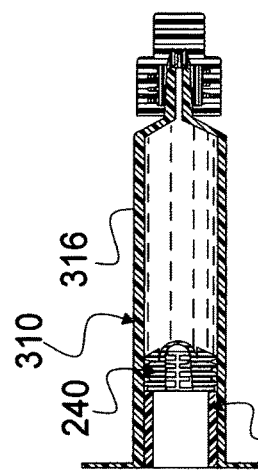
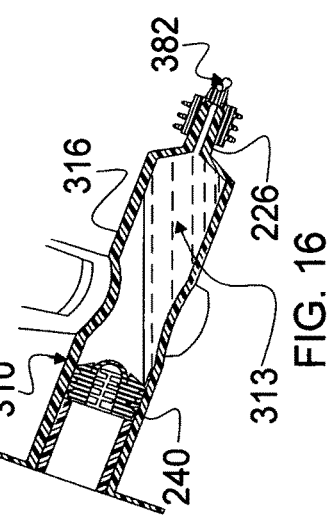

LIMITED STEP METHODS AND APPARATUS FOR MEDICINE STERILIZING AND BOTTLING

FIELD OF INVENTION

Inventions disclosed herein relate, generally, to convenience kits and associated applications for medical procedures involving steps for mixing, sterilizing and filling medicine containers which require being kept in a sterile state while being prepared and stored before use. Of particular note, similar to related art referenced, hereafter, convenience kits and methods of use, disclosed herein, are applied to preparation steps which can occur in a potentially contaminating environment and still produce a product sterilized to a desired sterilization assurance level (SAL). Therefore, the field of invention is particularly related to kits which are used to sterilize and, thereby, provide sterilized preparations in capped containers deliverable through non-sterile environments. Such kits employ sterilized, preassembled parts providing a protective enclosure (sterile chamber) which is sterile, closed and sealed having only a pathway or pathways into the apparatus through sterilizing filter assemblies which are primarily used for sterilizing fluids when displaced therethrough. As a result, a protectively packaged sterile product can be provided without requiring employment of a laminar flow hood or other sterilization assurance level product manipulating devices. More specifically, each kit made according to the instant invention disclosed herein is designed and fabricated to, generally, enable vessel filling with a fewer number of steps required to fill a given number of vessels than the number of vessels being filled. Each convenience kit is a single use tool which is specifically designed and assembled to be used in preparation of a particular medicine each time used.

RELATED ART REFERENCE

This patent application continues-in-part from U.S. patent application Ser. No. 17/300,842 and contains information related to U.S. Pat. No. 10,555,872 B2, U.S. Pat. No. 10,800,556 B2 and U.S. Pat. No. 10,940,087 B2 but includes inventive apparatus, methods, applications and singularity of scope, unforeseen and not previously disclosed therein by the inventors.

TABLE OF DEFINITIONS OF TERMS USED HEREIN fitting, n: a medical connector, commonly a luer fitting
SAL, n: Sterilization Assurance Level
substantially, adv: as nearly as possible

BRIEF SUMMARY AND OBJECTS OF THE INVENTION

In brief summary, this novel invention alleviates all of the known problems related to sterilizing a medical preparation, displacing into a capped vessel or container with a limited number of required steps before delivery for use. Such problems found in prior art consist of the number of steps and associated time required to:
a. Manipulate a spout within a bag to distribute drug to individual vessels.
b. Cap individual vessels disposed within a bag.
c. Displace a cap holding plate within a bag to position caps for attachment to close filled vessels.

Generally, novel approaches, for solving the problems by kits made according to the present inventions are:
a. Where possible, redefining vessel (e.g. a bottle) assembly to provide a pre-attached cap as an assembled unit before filling.
b. Filling all bottles simultaneously (single step) rather than one-by-one.
c. Using a closed sterile chamber which is not necessarily inside a plastic bag for preparation, delivery and containment.

Methods and apparatus, as disclosed hereafter, not only provide solutions for the above recited problems, but provide for new methods and apparatus for providing sterile preparations in ways not possible before. Solutions are found and provided by making convenience kits which utilize a first medical grade sterilizing filter for sterilizing medical preparations which are communicated into a manifold and thereby distributed to individual vessels provided as part of the delivered convenience kit. Where possible, the vessels are precapped and filled via valving which provides a barrier for sterility containment. All vessels and kit parts which can come into contact with the medical preparation during vessel filling are pre-sterilized. The first medical grade sterilizing filter and the manifold cooperate to provide a sterile pathway to each vessel. A stop provided for each vessel assures accurate dose amounts and as well being effective in avoiding overfill problems. All vessels within each kit are filled by a single dispensing action through the first medical grade sterilizing filter, thereby significantly reducing steps and other action required by kits defined in prior art. Generally, each manifold and associated vessels utilize fluid connectors which are luer compatible. Vessel capacity of a given kit can be increased by providing multiple manifolds which are serially interconnected and provided in either stacked or linearly aligned disposition. Each kit further provides for priming air from the communicating pathway in a pre-delivery mode and for returning undelivered medical preparation from the pathway which is replaced by air communicated through a second sterilizing filter in post-delivery mode. As well, the feature for returning unused medical preparation, resident in the pathway after filling vessels, permits evaluation of quality of the sterilized preparation by providing for a bubble test of the first medical grade filter at the end of the medical preparation return cycle. It should be noted that the opportunity for providing all medical preparation to be delivered via a stationary filter into vessels with filling stops significantly reduces steps and opportunity for dose dispensing errors.

It is therefore a primary object to provide a convenience kit made according to the present invention for providing a sterile preparation in an eye-drop dispensing vessel. It is a continuing object to provide an eye drop vessel made from a modified medical syringe made according to the present invention. It is another continuing and important object to provide an eye drop bottle made from a conventional eye drop bottle made according to the present invention.

It is another primary object to provide a convenience kit made according to the present invention for providing a sterile preparation in a medical syringe.

It is still another primary object to provide a convenience kit made according to the present invention for providing sterilized Avastin in silicone free syringes.

These and other objects and features of the present invention will be apparent from the detailed description taken with reference to accompanying drawings.

BRIEF DESCRIPTION OF THE DRAWINGS

FIG. 1 is a top elevation of a manifold often fittings made according to the present invention.

FIG. 1A is a top elevation cross section of a manifold of twelve fittings made according to the present invention.

FIG. 2 is an exploded top elevation of an Avastin convenience kit.

FIG. 3 is a top elevation of the Avastin convenience kit seen in FIG. 2, assembled.

FIG. 4 is a top elevation of an open clam shell case used with the Avastin convenience kit.

FIG. 5 is a magnified side elevation of a stop part used with the clam shell case, seen in FIG. 4, for determining fill quantities of Avastin in syringes.

FIG. 8 is a side elevation cross section of syringes modified according to the present invention for use in eye drop production and affixed to a section (seen in cross section) of a manifold before syringe filling.

FIG. 8A is an exploded cross section of the modified syringe seen if FIG. 8.

FIG. 8B is a side elevation of a plunger rod made for use in displacing pistons disposed in syringe barrels according to the present invention.

FIG. 9 is a side elevation of syringes, seen in FIG. 8, also in cross section and having been filled to a limit established by a stop in the barrel of each syringe.

FIG. 10 is an exploded view of the syringes, seen in FIG. 9, with one filled syringe detached from a straw used to communicate a medical preparation from the manifold.

FIG. 11 is a side elevation of the detached syringe seen in FIG. 10 with a plunger rod affixed to a plunger of the detached syringe.

FIG. 12 is a side elevation cross section of an eye drop bottle according to the instant invention.

FIG. 13 is an exploded view of the eye drop bottle seen in FIG. 12.

FIG. 14 is a side elevation cross section of the eye drop bottle seen in FIG. 12 filled with eye drop medication.

FIG. 15 is a side elevation cross section of a plunger used in eye drop and syringe vessels according to the present invention.

FIG. 15A is a frontal elevation of the plunger seen FIG. 15.

FIG. 15B is a side elevation of the plunger seen in FIG. 15 with a Pasteur filter disposed in a cavity thereof.

FIG. 15C is a top elevation of a superiorly disposed leaf (part) of the associated Pasteur filter seen in FIG. 15B.

FIG. 16 is a side elevation cross section of a filled eye drop bottle similar to the one seen in FIG. 14, with a cap removed and being digitally "squeezed" to produce a drop.

DETAILED DESCRIPTION OF THE ILLUSTRATED EMBODIMENTS

Figure 6:
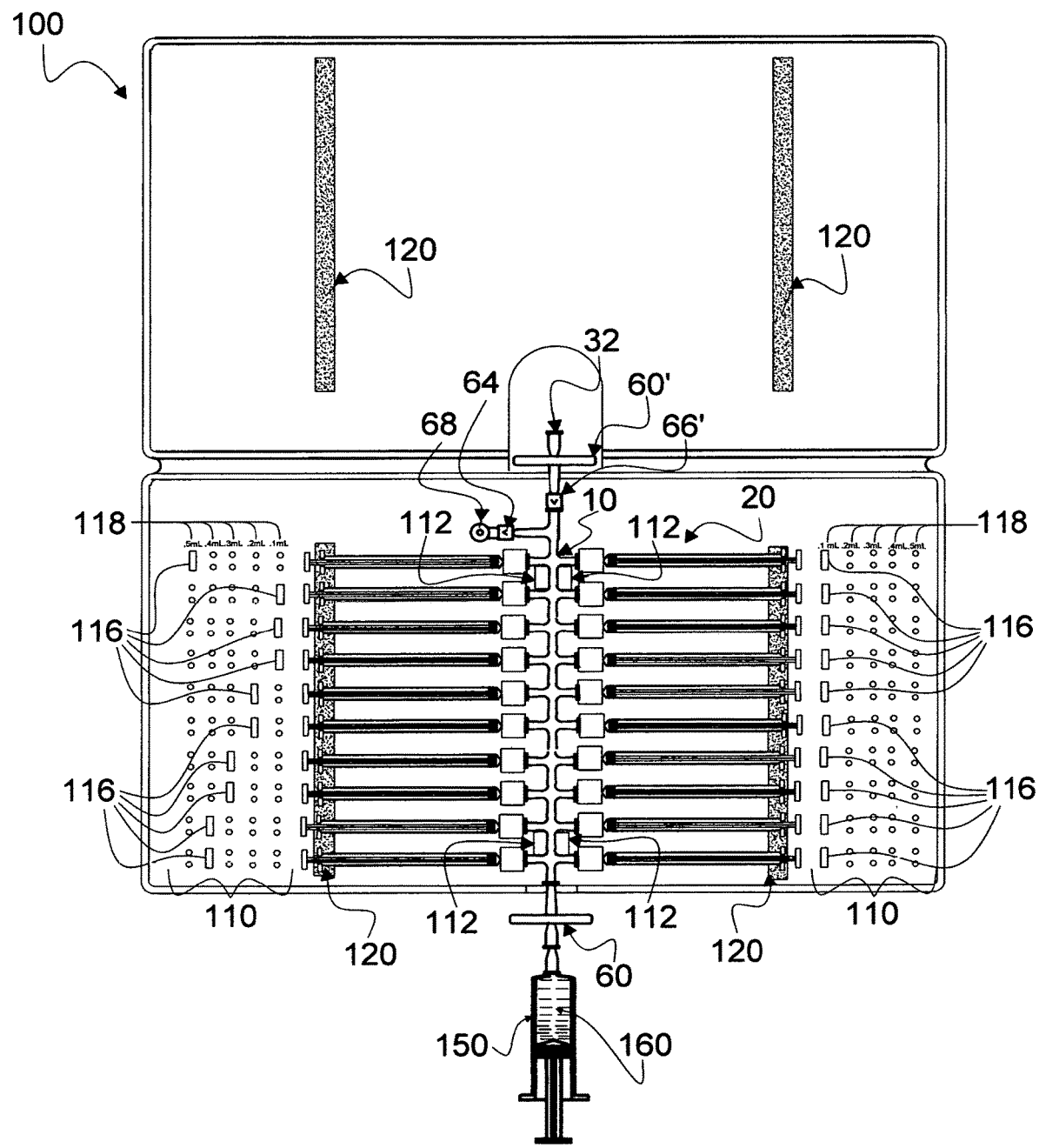
FIG. 6 is a top elevation of a convenience kit which may be used for compounding Avastin, utilizing the clam shell, seen in FIG. 4, with stops in place and in a ready state for receiving fluid.

In this description, the term proximal, when used, is to indicate the segment of the device normally closest to the object of the sentence describing its position. The term distal refers to the other end. Reference is now made to the embodiments illustrated in FIGS. 1-27 wherein like numerals are used to designate like parts throughout. Parts which are similar in form, function and use to the first numbered parts, but not identical, are designated with primed numbers of the first numbered parts.

The invention may be embodied in various specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Reference is first made to a manifold 10 seen in FIG. 1. Manifold 10 is a core item of the invention as the multiple fittings of a manifold coupled with a single pathway provides for filling a plurality of vessels with fluid communicated from a single source. Manifold 10 is preferably made by injection molding and laser bonding or 3D printing; however other manifolds, such as the manifold disclosed in U.S. patent application Ser. No. 17/300,842 can be used within the scope of the present invention. And so, it should be constantly kept in mind that prepared medicines sterilized and communicated into containers, for use in potentially contaminated areas, are commonly very expensive and any waste is costly to a convenience kit user, especially waste as a result of dead space. For this reason, a jointless, injection molded manifold, like manifold 10 is preferred. Processes for making such products as manifold 10 are well known and commercially contemporarily available.

Manifold 10, as seen in FIG. 1, comprises twenty luer shaped fittings, each numbered 30 and a volume-limited fluid pathway 32 (see manifold 10' in FIG. 1A) which is provided for communicating fluid there between. While a manifold can be made with almost any number of provided fittings and all manifolds are within the scope of the present invention, the cost of producing molds for a variety of manifold applications makes number of medication delivery fittings available an important issue. The number twenty four of fittings in manifold 10', seen in FIG. 1A, was selected for some exemplary convenience kits disclosed herein because of the many lesser numbers which can be profitably used, such as 12, 8, 6, etc. when larger vessels are to be filled with a single manifold used in different convenience kits. On the other hand, the number 10 is conducive to be used for providing Avastin in a syringe due to compliance with purchased volumes of concentrated medicine. Even though extra fittings are available when comparing manifold 10' to manifold 10, it should be noted that unused fittings can be capped for manifold applications which use fewer than the supplied number of fittings thereby providing opportunity for making a plurality of convenience kit applications using a single manifold design.

Before further disclosing exemplary convenience kit applications, it is considered important and necessary to review basics of the instant invention. As disclosed supra, the purpose of each kit, made according to the present invention, is to provide a convenience kit which can be used in a potentially contaminating environment, to provide for sterilizing medical preparations initially prepared outside the kit and filling vessels with medical preparations sterilized to a predetermined SAL. It is important that such medical preparations be not only sterilized, but kept appropriately sterile until accessed for use.

As presently available kits are quite labor intensive, requiring individual, sometimes arduous, steps in filling and capping, it is therefore an inherent object of the present invention to provide novel methods and apparatus which produce at least equal results, i.e. accomplishing the same purpose of earlier kits with significantly fewer and easier steps. In other words, inventive methods and apparatus based upon the instant invention should not only assure that medical preparations are delivered sterile to the point of use, but, to the extent possible, significantly reduce the number of required steps involved in kit use. All convenience kits, made according to the present invention, are provided presterilized and, using fluid tight fittings, maintain internal pathways and other sterile chambers at a desired level of sterilization throughout medical preparation processing and storage.

1. Avastin Application:

A first exemplary application for using manifold 10 is providing syringes filled with Avastin as disclosed in FIGS. 2-6. Therein, manifold 10 is used as the core item of a convenience kit 20. As each fitting 30 is shaped and sized for luer interface, small syringes commonly numbered 40, can be affixed, fluid tight, thereto as seen in FIG. 3.

Figure 7:
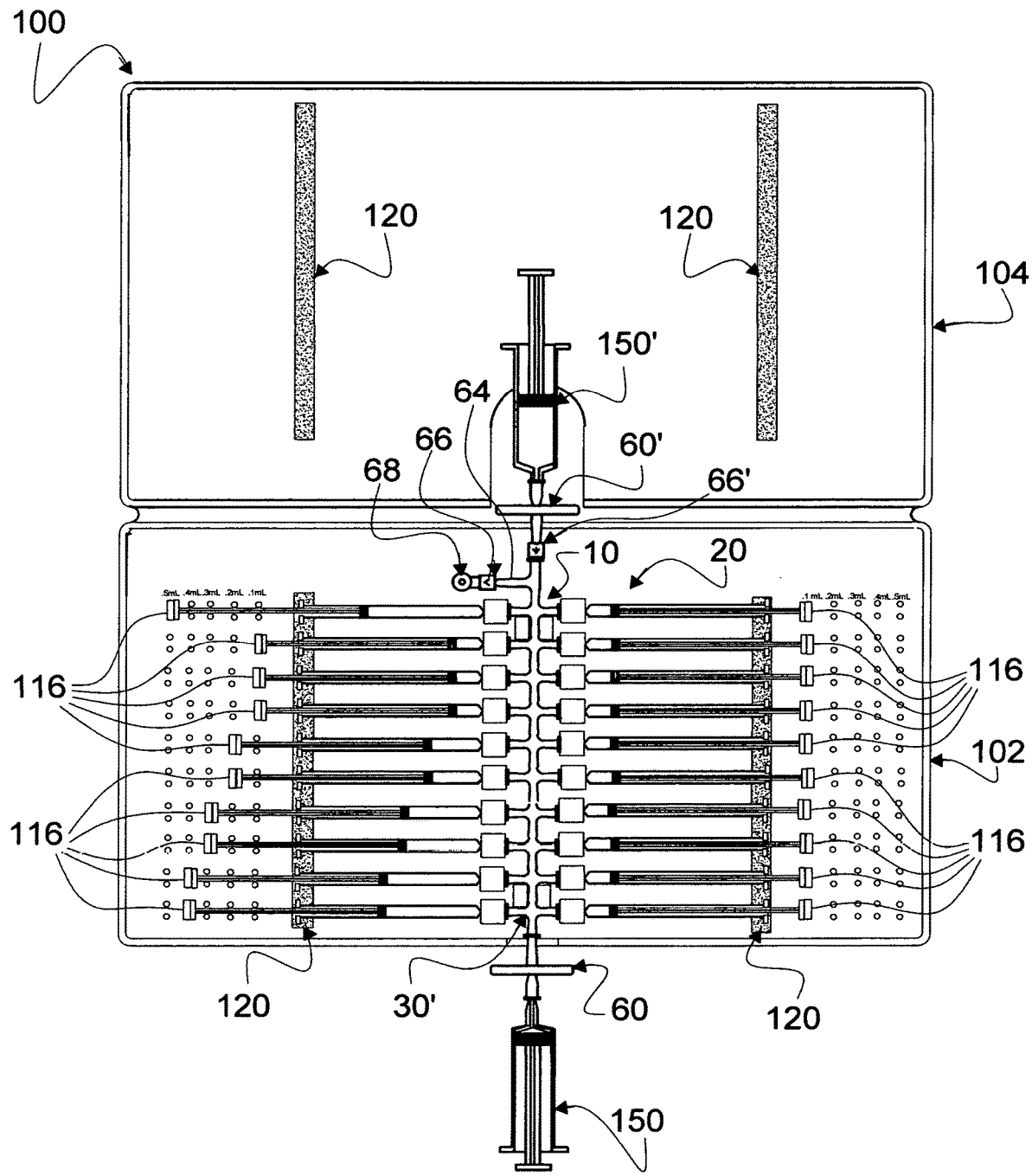
FIG. 7 is a top elevation similar to the top elevation seen in FIG. 6, but with syringes filled, each syringe containing a dose volume determined by stop settings.
Figure 19:
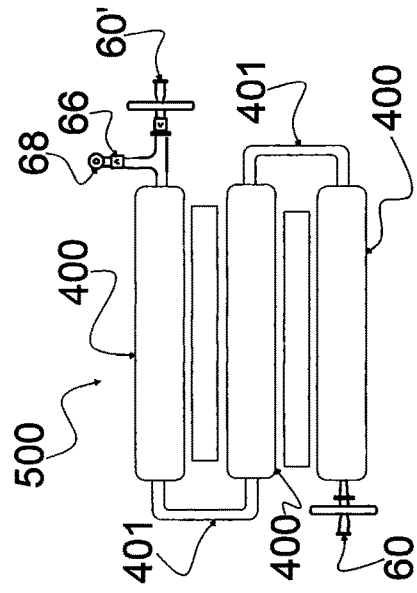
FIG. 19 is a block diagram disclosing a stacked convenience kit made according to the instant invention.

In an Avastin convenience kit made according to the instant invention, a plurality of syringes (commonly numbered 40) are disposed to communicate with pathway 32 (see FIG. 1A). However, if a syringe 40, after being filled is displaced from manifold 10, pathway 32 is opened into what might be a contaminating environment. For this reason, needleless connectors, commonly numbered 50, are used as an interface between each syringe 40 and manifold 10 for closing access to sterile pathway 32 within the manifold, permitting each filled syringe 40 to be independently displaced from the manifold 10 without compromising sterility of syringes 40 remaining affixed thereto. Therefore, each such needleless connector 50, as seen in FIGS. 6 and 7, is affixed between each preparation communicating fitting 30 and a syringe 40. Repeating, by so doing, an individual syringe 40 can be displaced from kit 20 without permitting an influx of contaminating fluid into an adjoining pathway to thereby provide maintenance of an uncompromised sterile chamber, wherein fluid communicated to each syringe 40, is kept sterile when other syringes are displaced therefrom for use.

As seen in FIG. 2, parts to be assembled for kit 20 comprise manifold 10 having twenty fittings (each numbered 30), a first medical grade filter 60 which is provided to be affixed to manifold 10 fitting 30' disposed as seen in FIG. 2, a one-way valve 64 which is provided to be affixed to manifold 10 fitting 66, a fluid state valve 68 to be affixed to one-way valve 64, another one-way valve 64' to be affixed to a manifold 10 fitting 30", a second medical grade filter 60' to be affixed to one-way valve 64' and twenty Avastin compatible syringes (each numbered 40) to be affixed to communicate with twenty-four needleless connectors (each numbered 50), each of which is to be affixed to an associated manifold 10 fitting 30.

As seen in FIG. 3, for sterilizing a medical preparation before entry into the previously sterilized pathway 32 and being communicated to each syringe 40 (also presterilized), medical grade filter 60 is securely and affixed fluid tight to a manifold 10 fitting 30'. In addition, at the opposite end of manifold 10 from fitting 30', an extended molded portion 62 provides a male luer fitting 64 and a female fitting 30" which also communicate with the pathway 32 disclosed supra. A one-way valve 66, disposed to permissively permit flow from the pathway, is affixed to male fitting 64. A state dependent valve 66, which is permissive to gas flow, but occlusive to liquid flow, is affixed to male fitting 64 to permit for pathway priming of air from pathway 32. The second medical grade filter 60' is affixed to one-way valve 66' which is further affixed to fitting 30" to thereby permit only sterilized air being displaced into the sterile chamber formed within pathway 32 when pressure differentials so dictate. Each syringe 40 is affixed to a needleless connector 50 which is securely affixed to a manifold 10 fitting 30. Once fully assembled, as seen in FIG. 3, kit 20 is sterilized to a predetermined SAL such that all parts and pathways, susceptible to contamination, are adequately protected through syringe filling and displacement via pathway 32 in manifold 10 in which fluid can only enter through sterilizing filters 60 and 60'.

With all fittings joined, as seen in FIG. 3, kit 20 is nearly ready for filling except for the consideration that filling is not at a standard rate to all syringes. Because filling is not controllable nor at the same rate for every syringe 40 and different dose volumes might be desired to be communicated into each particular syringe 40, for all syringes to be filled from a single actuated source, each individual syringe 40 must have a limiting stop to assure culmination of correct dosage in each syringe 40. Stops are, therefore, used to assure each syringe will be controlled to a predetermined dose volume independent of fill rate.

A case 100, seen in FIG. 4, is provided as a tool used for filling syringes using convenience kit 20. As seen in FIG. 4, case 100 comprises a clam shell configuration comprising a bottom compartment 102 and a top compartment 104. Bottom compartment 102 has two arrays of pairs of holes, each numbered 110, and manifold 10 positioning supports, each numbered 112, which provide for accurate displacement of manifold 10 into bottom 102 of case 100. The holes in each array 110 are disposed to provide a place for a stop 116 (see FIG. 5) to be inserted thereat to retard plunger displacement and, thereby, filling volume in each specific syringe 40.

Indicia 118 at the top of each column of holes in each array 110, provide notice of filling volumes specified by insertion of a stop 116 into related pairs of holes. Note, in each stop 116, seen in FIG. 5, are two insertion rods 117 and 117' which are sized and spaced to fit into each of two holes in each row, aligned to selectively provide the so designated stop 116.

The major reason for a clam shell configuration for case 100 is better understood by disclosure seen in FIG. 6 where a convenience kit 20 is seen to be displaced into a case 100. Some Avastin syringes do not have luer lock fittings, but rather luer slip fittings. As filling syringes 40 is the result of flow from a pressurized source, care must be take in assure no syringe is displaced from communication with pathway 32 due to filling pressure. For this purpose, four strips of foam tape (each numbered 120) being sufficiently thick to engage finger engaging flanges on the barrel of each syringe 40 when the clam shell case 100 is closed to thereby provide a force which holds each syringe 40 in place while filling. Also, all connections within convenience kit 20 are affixed fluid tight such that the only fluid entry into pathway 32 is through medical grade filters 60 and 60' which thereby retain pathway and all connected parts in a desired sterile state.

Preparatory to filling syringes 40 with prepared medicine, a syringe 150 filled with a medicine preparation 160 is affixed to filter 60, as seen in FIG. 6. Case 100 at this point is normally closed. However, for clarity of presentation, case 100 is seen open in FIG. 7, with all syringes 40 having been filled with a desired volume of medicine preparation 160 with a single stroke of syringe 150. However, before delivery of such medicine to each syringe 40, pathway 32 (see FIG. 1A) should be purged of air and primed. For this reason, one-way valve 66 and state valve 68 are disposed to permissively release gas from pathway 32 and then close to increase liquid pathway 32 delivery pressure. Note that, one-way valve 66' also closes pathway 32 which results in a liquid pressure in pathway 32 which acts to fill each syringe 40 (see FIG. 3) with sterilized medicine preparation. Note that stops 116 restrict displacement of syringe 40 plunger rods to provide for filling each syringe 40 to a predetermined volume.

When filling from syringe 150 is complete, syringe 150 can be used to draw sterilized liquid remaining in pathway 32 back into syringe 150 through filter 60 for future use. Further, a syringe 150' filled with air, affixed to filter 60' can be used to force liquid resident in needleless connectors 50 (see FIG. 3) into syringes 40. In this manner, all liquid, except for a small amount retained in male fitting 64 can be purged from pathway 32. At this point, each syringe 40 can be displaced from kit 20 without degrading sterility of remaining syringes 40. Further, drawing air to filter 60 causes a change of state of fluid at filter 60 and filter 60 is not open for gas transmission when wet. Thus, a "bubble test" is provided thereby to assure filter 60 is not damaged to the point of being permissive to unfiltered fluid flow and no longer an effective filter.

2. Filling Syringes for Conventional Syringe Use

Figure 20:
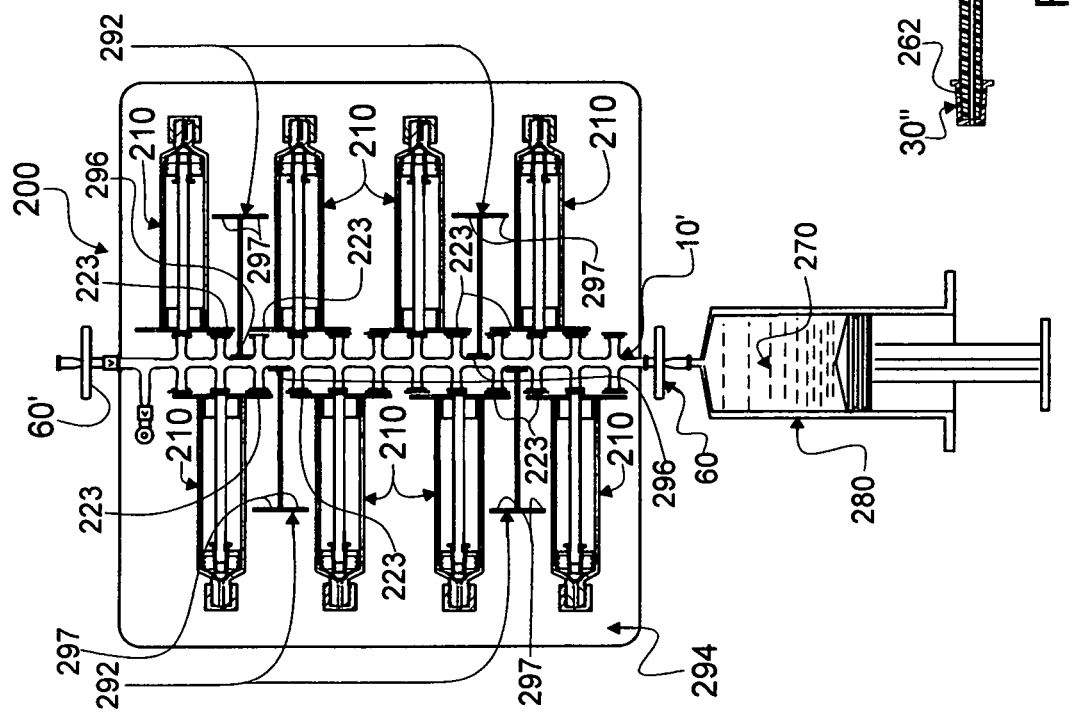
FIG. 20 is a cross section of a syringe filling kit made according to the present invention whereto a filled source syringe is affixed to a first medical grade filter for filling empty syringes.

Reference is now made to FIG. 20 wherein a convenience kit 200 made according to the instant invention is seen. As seen in FIG. 20, convenience kit 200 can be made using a manifold 10' fitted with filters 60 and 60'. Vessels used in convenience kit 200 are syringes, each numbered 210. Each syringe 210, as is common for medical syringes and seen in FIG. 8A, comprises a barrel 220 of substantially constant diameter throughout it length. Further each syringe 210 comprises an open end 222 through which a plunger (or piston) is inserted and by which syringe is held by finger flanges, each numbered 223, and a diminished end 224, closing to a fluid communicating spout 226. Each syringe is, generally, capped with a cap 212 affixed in fluid-tight relationship to a syringe barrel 220 spout 226. Disposed within each barrel 220, in inventions made according to the instant invention, is a piston 240 (sometimes referenced as a plunger, herein). For safety, a stop cylinder 250 is also optionally provided and securely affixed at open end 222 to assure filling does not exceed syringe 210 capacity.

Syringes, used as vessels which are filled by apparatus and methods consistent with the instant invention disclosed herein, differ from conventional syringes in the design and structure of piston 240. While it is common for a plunger to be used within a syringe barrel, it is not common practice to pre-fill barrels of syringes with both a cap and a plunger in place. However, doing so provides a method for sterilizing and filling liquids displaced into vessels without requirement for capping thereafter, thus reducing steps required for producing a convenience kit wherein a vessel (in this case syringe 210) is filled with sterilized liquid and provided for use without additional preparatory steps.

Reference is now made to FIG. 15 wherein a piston 240 is seen. While piston 240 comprises a body comprising a series of wall interfacing rings (generally numbered 242) which are customarily used for wiping fluid away from walls of a syringe when displaced there through, medially disposed, relative to rings 242, is a dome shaped portion 250 which comprises a slit 252, sized and disposed for providing a one-way valve thereby. Disposition of dome shaped portion 250 and slit 252 are better seen in FIG. 15A. So disposed, portion 250 acts as a one-way valve, permissive to flow toward the capped end of syringe 210. On a side of valved piston 240, opposite dome shaped portion 250, is a specially shaped cavity 254 made such that a male luer fitting can be affixed in fluid tight relationship with piston 240 for the purpose of displacing piston 240 and associated liquid thereby.

Reference is now made to FIGS. 8-11 wherein a syringe filling-to-readiness-for-use process is disclosed. As seen in FIG. 8, two empty syringes 210 are each affixed via a straw 260 (see FIG. 22 for details of design according the instant invention) to a fitting 30 for communicating with pathway 32 of a manifold 10' (see FIG. 1A).

Figure 22:
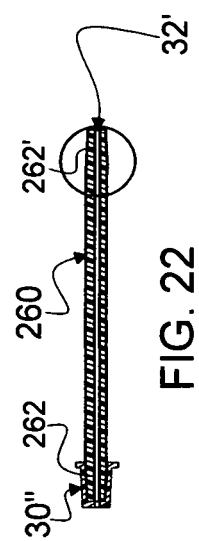
FIG. 22 is a magnified cross section of a straw used for communicating liquid from a manifold to a syringe part.

As seen in FIG. 22, straw 260 is preferably a semi-rigid tube having a very small (micro) diameter pathway 32' there through. A fitting 30" can be provided on one end or both ends (each numbered 262) of straw 260 for communicating in fluid-tight relationship with manifold 10' on one end and an associated valved piston 240 on the other end. As such, each straw 260, comprises an inherent pathway 32' which becomes an inherent part of pathway 32 for communicating fluid to piston 240 and therefrom into an associated barrel 220 to provide for filling a plurality of syringes simultaneously from a single source. As the plurality of syringes are likely to be affixed to a manifold, production time and cost must be considered. For this reason, an end 262 associated with being affixed to a plunger 240 (see FIGS. 12-16) should be easily affixed thereto, securely for filling, but releasable for use. For this purpose, a "push-on/twist-off" fitting 264 is provided at an end 262 (i.e. end 262') for affixing and releasing plunger 240 (and an associated vessel) from being affixed to and communicating with pathway 32'.

Figure 22A:
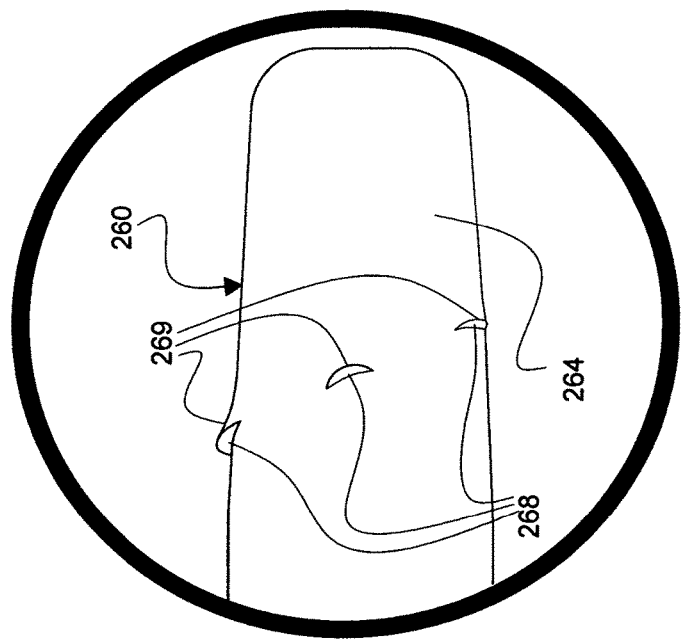
FIG. 22A is a further magnified top elevation of the portion of the straw seen in FIG. 22 enclosed by a circle about one end.

An example of fitting 264 is seen in FIG. 22A. A pattern 266 of barbs are molded directly to fitting 264, each such barb comprises a barrier 268 comprising a sharpened edge 269 which digs into plunger 240 to oppose displacing plunger 240 from fitting 264 by pulling. Further, barb pattern 266 which comprises a line of sharpened edges 269 which define a "thread pattern" like that of a screw which is permissible to displacement by twisting or rotating plunger 240 relative to fitting 264 such that an associated vessel can be removed for use.

As seen in FIG. 9, two syringes 210 are so filled with liquid 270, which has been passed through filter 60 to be thereby sterilized. Note that sterility of liquid 270 is retained by closure of slit 252 (see FIG. 15A) when a filled syringe 210 is removed from straw 260, as seen in FIG. 10. At this point, a syringe plunger rod 280 (seen alone in FIG. 8B) can be affixed to syringe as seen in FIG. 11 for delivery for use into a potentially contaminating environment with assurance of liquid 270 being maintained and provided at a predetermined SAL.

Figure 21:
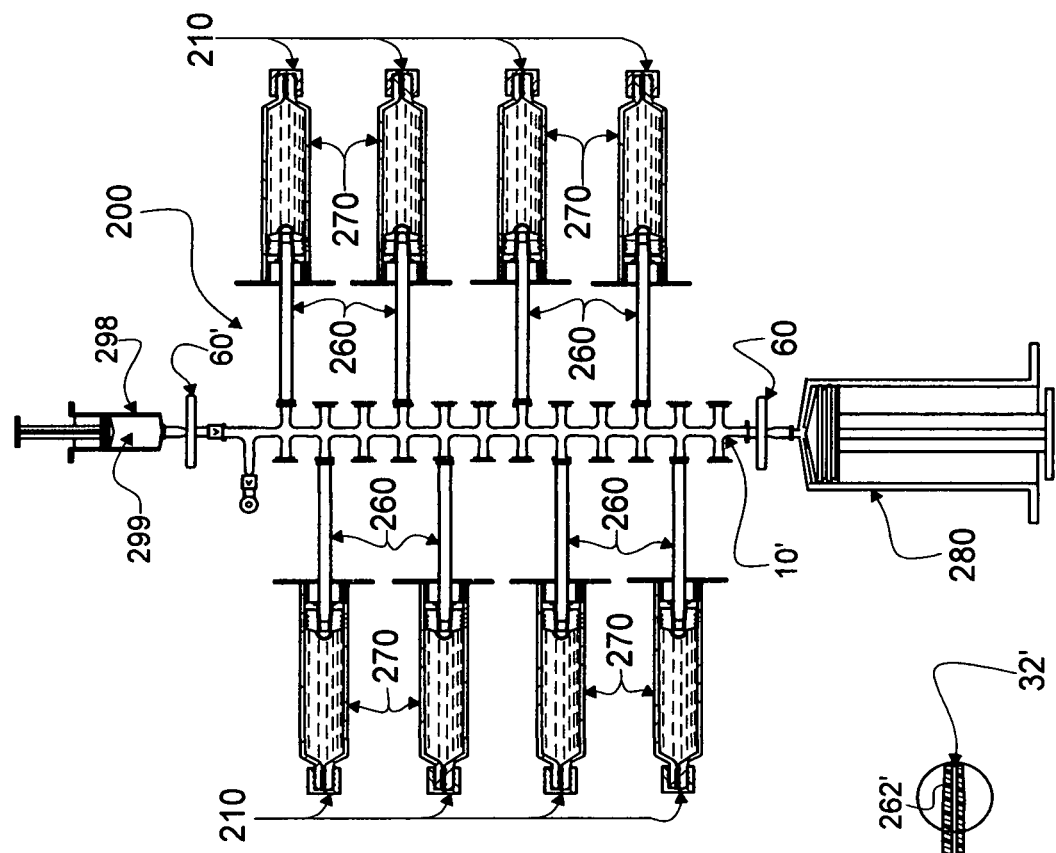
FIG. 21 is a cross section of the syringe filling kit seen in FIG. 20 with the source syringe emptied to thereby provide medication for filling syringes affixed to an associated manifold.

Reference is now made to FIGS. 20 and 21 where all syringes 270 are first seen empty in FIG. 20 and then concurrently filled by a single action of dispensing liquid (e.g. a prepared medication) through a filter 60 as seen in FIG. 21 which sterilizes liquid 270 being concurrently dispensed into the plurality of syringes 210. For clarity of reference to parts of syringe 210, reference is made to FIG. 8. Each syringe 210 comprises a substantially constant diameter barrel 220, a plunger or piston 240 (see FIGS. 15 and 15A), a plunger stop 222 disposed in barrel 220 and a spout 226 which is seen closed by a cap 212.

Returning to FIG. 20, note a framework, commonly numbered 292 and securely disposed on a work-plate 294, provides stabilizers 296 for manifold 10' and stops 297 for finger tabs 223 (see FIGS. 8 and 21), stops 297 being provided for determining fill volumes by limiting displacement of an associated barrel 220 of each filling syringe 210.

In FIG. 21, convenience kit 200 is removed from workplate 294 and liquid 270 initially disposed in syringe 280 has been displaced, via a single act using syringe 280, into all syringes 270. A second syringe 298, filled with air 299, is affixed to filter 60' for the purpose of dispensing air 292 into manifold 10' pathway 32 and straws 260 to purge liquid therefrom. With air in pathway 32, an effective "bubble test" can be performed on filter 60 to prove filter performance adequacy, as is well known and understood in medical art where filters are used for sterilizing liquid.

3. Modified Syringes for Eye Drop Bottle Use According to the Present Invention

Figure 17:
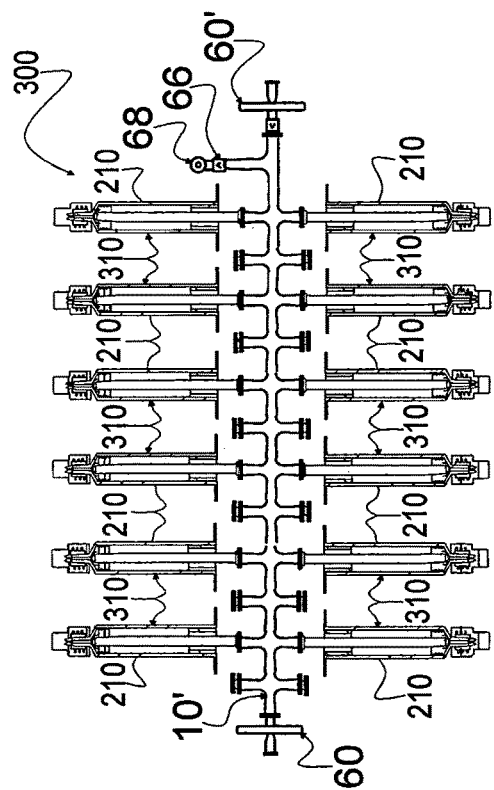
FIG. 17 is a top elevation cross section of a plurality of eye drop bottles affixed to a manifold to form a convenience kit according to the present invention.

Reference is now made to FIG. 17 wherein an eye drop bottle kit 300 is seen to comprise manifold 10' and twelve eye drop bottles, each numbered 310 and made according to the instant invention. The same manner of filling syringes according to the instant invention is used for filling syringes modified for use as eye drop bottles. For this reason and for applying bottle filling disclosure to the modified syringes, the same numbers are used herein for numbers previously used for syringes (e.g. 210). The resulting syringe apparatus modified for use in an eye drop preparation convenience kit are numbered 310.

An eye drop bottle 310 affixed to a straw 260 is seen in FIG. 12. Parts used in assembly of eye drop bottle 310 are seen in FIG. 13, wherein stop 250, piston 240 and syringe barrel 210 can be the same parts as those used in syringe filling according to the instant invention. However, barrel thickness and material may be varied to better meet requirements for producing eye drops. As seen in FIG. 16, rather than displacement by a plunger rod, eye drops are engendered by squeezing a syringe barrel 220, containing eye drop liquid 313. For this reason, eye drop bottle material should be selected which is sufficiently elastic to permit drop production by squeezing, but also sufficiently resilient to reactively resume a prior shape at the end of eye drop production. Such material (for example LDPE) is currently available commercially.

As seen in FIG. 13, major differences between syringe and syringe modified eye drop configurations are an eye drop adapter 320 and an eye drop bottle cap 330 used instead of a syringe cap, previously numbered 212. Cap 330 can be a cap already in manufacture and use for eye drop production devices using prior geometry. Eye drop adapter 320 then should comprise cap attachment means, such as molded threads 340 which are compatible with a thread attachment of cap 330. Further, eye drop adapter 320 should have a cavity 350 which fits in fluid tight relationship with spout 226 of syringe barrel 220 and have drop producing geometry consistent with production of drops of a predetermined size. Such geometry is well known in the eye drop production art. An "as-filled" eye drop bottle 310, filled with eye drop solution 360 is seen in FIG. 14.

Rather than replacing used eye drop volume with air drawn in through an eye drop spout, availability of the one-way valve characteristic of plunger 240, a Pasteur filter 370 can be inserted into cavity 254 as seen in FIG. 15B. As is well known, a Pasteur filter is a very effective gas filter which is made by providing a series of cavities interconnected by out-of-line, very small holes. The Pasteur filter 370 should be designed such that each small hole (i.e. each hole made by notches 374, 376, 378, 379 and 380 seen in FIG. 15B) in each successive plate that is used to make up the filter provides the only fluid access through the filter. An exemplary top plate 372 with a notch 374 for a hole is seen in FIG. 15C. Successive notches 374, 376, 378 and 380 are seen in FIG. 15B.

As seen in FIG. 16, an eye drop 382 is produced by squeezing barrel 220 between piston 240 and spout 226 in the same manner a commercial eye drop bottles are used.

Figures 23, 24, 25:
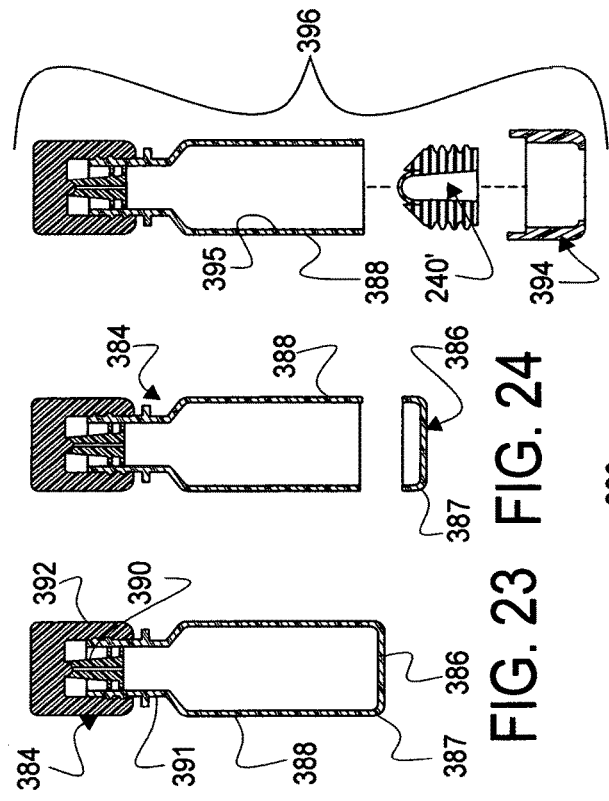
FIG. 23 is a cross section of a conventional eye drop bottle.
FIG. 24 is a cross section of the conventional eye drop bottle seen in FIG. 23 with a bottom part severed from a barrel of the bottle.
FIG. 25 is an exploded cross section of the bottomless eye drop bottle seen in FIG. 24, a valved piston seen in cross section and a bottle extender/stop part also seen in cross section.

3. Modified Eye Drop Bottles for Eye Drop Bottle Use According to the Instant Invention Of practical concern is size and shape of eye drop bottles in common use today. There are many patients who use eye drops on a regular and extended basis. For this reason, it is particularly important to modify a conventional eye drop bottle for use in convenience kits made according to the present invention. For example, such an eye drop bottle 384 is seen in FIG. 23. Generally, each such eye drop bottle 384 comprises a substantially flat bottom 386 affixed via a curved surface 387 to a cylindrical barrel 388 of substantially constant diameter, and a liquid outlet drop producing spout 390, disposed in a neck 391 of bottle 384, which is closed and sealed by a cap 392.

Figures 26, 27:
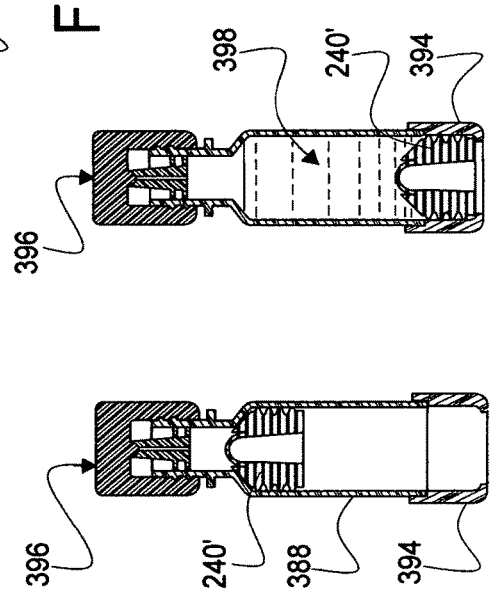
FIG. 26 is a cross section of an assembled modified eye drop bottle made according to the instant invention.
FIG. 27 is a cross section of the modified eye drop bottle seen in FIG. 26 with the barrel displaced relative to the valved piston due to filling of the eye drop bottle with eye drop medicine.

As seen in FIG. 24, the first step in eye drop bottle modification is severing the bottom 386, including the curved surface 387 from the barrel 388. As seen in FIG. 25, a valved piston 240' and a bottle extender, piston stop part 394 are sized and shaped to wipe fluids from the inner wall 395 of barrel 388 and provide an extended volume of barrel 388 for a bottle 396 and a stop for piston 240' (see FIG. 27), respectively. A completed assembly of a modified eye drop bottle 396, as seen in FIG. 26 with piston 240' fully displaced into barrel 388 and part 394 securely affixed in fluid tight relationship to barrel 388.

Eye drop bottle 396 is then employed as part of a convenience kit similar in form and function to kit 200 seen in FIG. 20 where, in this example, modified eye drop bottles 396 are provided, as vessels to be filled, rather than syringes 210. The associated process of sterilizing an eye drop preparation 398 (see FIG. 27) is by using same procedure disclosed for FIGS. 8 and 9 and FIGS. 20 and 21 with a syringe 210 being replaced by a modified eye drop bottle 396 in a kit, not numbered herein, but as numbered 200 for syringe applications. In other words, each eye drop bottle 396 piston 240' is affixed in a kit, like kit 200, to a straw 260 which is affixed to a manifold 10'. Manifold 10' provides a pathway 32 for communicating liquid preparation from a single source (e.g. a syringe 280) to each so affixed modified eye drop bottle 396. As such, each modified eye drop bottle 396 is sterilized as the rest of the kit associated with bottle 306 is sterilized. Preparation 398 dispensed into modified eye drop bottle 396 is sterilized before entry into manifold 10' pathway 32 by filter 60. Other features, such as those provided by filter 60' and state valve 68, disclosed in syringe 210 applications, are also provided for modified eye drop bottle 396 applications.

5. Using Linked Kits to Improve Bottle Filling Efficiency

Figure 18:
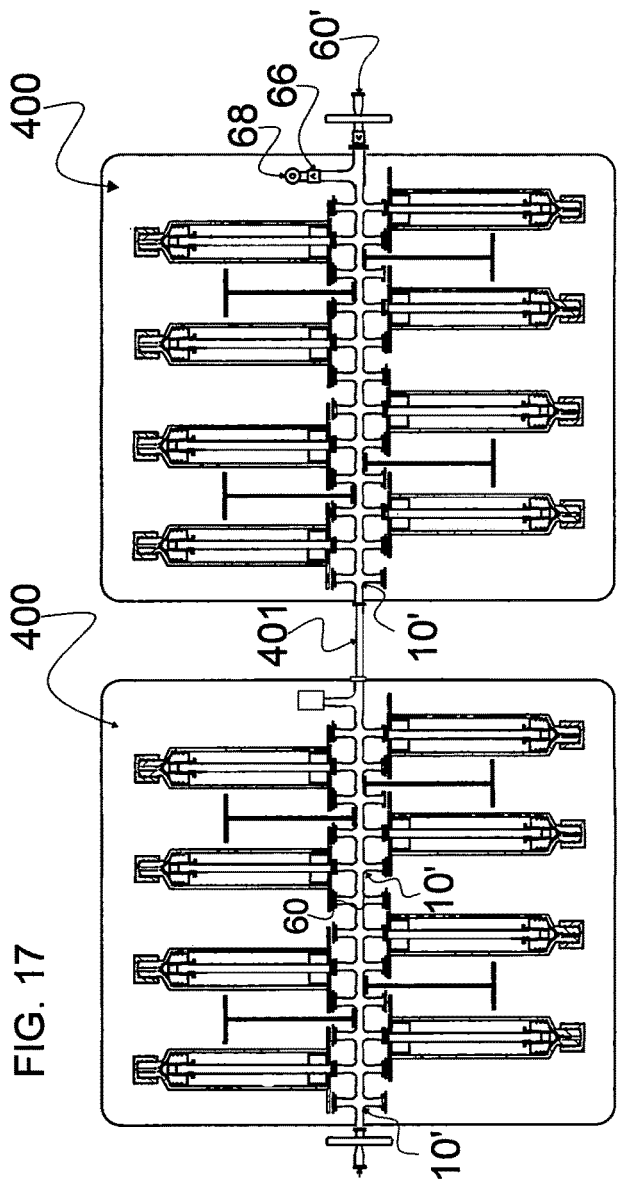
FIG. 18 is a top elevation of two eye drop convenience kits made according to the present invention serially linked for operation as a single unit eye drop vessel filling convenience kit.

While sterilizing and filling pre-capped vessels is significantly more efficient than prior art methods which require individual steps for both filling and capping, overall efficiency is limited by the number of vessels affixed to a fitting limited manifold of a convenience kit. However, due to the nature of filling by kits made according to the instant invention, multiple individual-manifold kits can be serially linked or ganged almost limitlessly as seen by example in FIGS. 17 and 18. In FIG. 17, two kits, each exemplary kit being numbered 400, although such an extension also applies to other convenience kits such as kits 200 and 300, as well, are serially linked to operate as one. Note, at only the most remote kit from the kit to which filter 60 is affixed is an assembly of filter 60' and associated priming devices required. Such is the case for all kits joined in sequence. A convenience kit 500 comprising a stack of convenience kits, similarly interconnected, is seen in FIG. 18.

What is claimed and desired to be secured by Letters Patent is:

1. A method for providing and using a convenience kit for sterilizing and concurrently communicating a desired volume of liquid medication into each of a predetermined number of vessels, which have been pre-sterilized before receiving the sterilized liquid medication, such that a predetermined volume of liquid is displaced into each vessel from a single source through a sterilizing filter, thereby providing a medical preparation sterilized to a desired predetermined SAL which can be delivered via capped and closed vessels into a potentially contaminating environment without compromising the sterility thereof, comprising the following steps:

a. providing said convenience kit comprising a first medical grade sterilizing grade filter affixed to an associated manifold comprising a closed pathway, there through, said first sterilizing filter being affixed to a manifold connecting interface disposed at a proximal end of said manifold to provide for fluid tight liquid delivery communication into and through said closed pathway within said manifold to a plurality of inherent manifold fittings, each manifold fitting being fabricated with attachment features for securely but releasably connecting each vessel in fluid tight communication with said manifold for the purpose of being so filled;

b. providing said predetermined number of vessels and securely but releasably affixing each vessel to communicate in fluid tight relationship with the manifold as a part of said convenience kit, each of said vessels comprising variable capacity for receiving and storing the predetermined volume of liquid;

c. affixing a cap to any manifold vessel inherent fitting which is not used for communication with a vessel such that the pathway is closed thereat;

d. sterilizing said convenience kit to a predetermined SAL;

e. providing a source of the liquid medical preparation in a container used for communicating the medical preparation through said first sterilizing grade filter into the pathway and through the fittings into each vessel and, thereafter, for withdrawing surplus liquid through said first sterilizing filter;

f. providing an individual stop for each vessel affixed to the manifold to assure a predetermined volume of the medical preparation is communicated to each vessel; and g. displacing liquid from the container into the manifold, thereby, communicating the predetermined volume of the sterilized medical preparation at a predetermined SAL into each pre-sterilized vessel through a sterilized pathway into closed containers all of which can be filled via a single container dispensing step.

2. The method for providing and using a convenience kit for sterilizing and communicating a desired, selectively determined volume of liquid medication into each of a predetermined number of vessels, according to claim 1 wherein said providing step of a first medical grade sterilizing grade filter being affixed to an associated manifold comprises a stationary attachment between said sterilizing grade filter and said manifold.

3. The method for providing and using a convenience kit for sterilizing and communicating a desired, selectively determined volume of liquid medication into each of a predetermined number of vessels, according to claim 1, further comprising providing a bifurcated fitting providing two outlet connections for the pathway being affixed in communication with the distal end of said pathway in said manifold before said sterilizing step.

4. The method for providing and using a convenience kit for sterilizing and communicating a desired, selectively determined volume of liquid medication into each of a predetermined number of vessels, according to claim 3, further comprising providing, before said sterilizing step, a first one way-valve, with freedom of flow only into the pathway being affixed to a first outlet of the bifurcated fitting for being interposed between the pathway and a second medical grade filter and a second one-way valve affixed to a second outlet of the bifurcated fitting with freedom of flow only out of the pathway and being serially affixed to a fluid state sensitive valve which selectively permits gas to flow from the pathway but retards all liquid flow therefrom for the purpose of priming air from said pathway.

5. The method for providing and using a convenience kit for sterilizing and communicating a desired, selectively determined volume of liquid medication into each of a predetermined number of vessels, according to claim 4, whereby the displacing liquid from the container into the manifold step first purges gas from the closed pathway via the state sensitive valve by selectively permitting gas to flow from the pathway, but retarding all liquid flow therefrom.

6. The method for providing and using a convenience kit for sterilizing and communicating a desired, selectively determined volume of liquid medication into each of a predetermined number of vessels, according to claim 5, whereby, after completion of the displacing liquid from the container into the manifold step for the purpose of filling the vessels, said step of dispensing flow is reversed, and a following step comprises drawing air through the second medical grade filter into the manifold pathway and to the first medical grade sterilizing grade filter until air is communicated to the first medical grade filter, at which time due to a significant increase in fluid transmission resistance through first medical grade sterilizing grade filter is used for indicating liquid has been purged from the pathway and, via a bubble test, the first medical grade sterilizing grade filter is operating properly.

7. The method for providing and using a convenience kit for sterilizing and communicating a desired, selectively determined volume of liquid medication into each of a predetermined number of vessels, according to claim 1, wherein the vessels providing step comprises providing a plurality of capped medical syringes and associated filling straws, each such syringe comprising a barrel, comprising a large, open end where commonly a plunger rod is disposed, and a valved plunger piston comprising a one-way valve which is disposed for permitting fluid to flow into a barrel of each said syringe from the large, open end of said barrel, said valved plunger piston being displaced to be resident within a displaceable portion of an associated syringe barrel to form a limited dead space between said piston and an associated syringe fluid communicating spout, each of said valved plunger pistons further comprising a straw fitting which communicates with the plunger one-way valve such that fluid flowing from a filling straw affixed to a filling straw fitting permissively flows through the piston valve toward the spout which is closed by a cap and further comprises an assembly step of affixing the filling straw to an inherent manifold fitting and to a piston valve straw fitting while disposing the associated plunger piston at the far end of the syringe of each so affixed syringe away from the inherent manifold fitting.

8. The method for providing and using a convenience kit for sterilizing and communicating a desired, selectively determined volume of liquid medication into each of a predetermined number of vessels, according to claim 7, further comprising the following steps for using a sterilized convenience kit made according to the present invention:
   a. provide the container filled with an appropriate volume of prepared liquid medication and affix the container to said first sterilizing filter;
   b. with a single continuous act, dispense the liquid medication through the first sterilizing filter thereby purging gas from the pathway and then dispensing liquid medication through the pathway and straws into each syringe via an associated piston valve which displaces each associated syringe barrel as the liquid medication is delivered therein and continues barrel filling until a stop retards barrel displacement and further filling;
   c. after all syringes are so filled, perform a further step of providing a syringe piston rod for each syringe and, when each syringe is detached from a straw, affix the syringe piston rod to the straw fitting for conventional syringe operation of dispensing the liquid medication kept at the predetermined medical preparation SAL until the cap is removed.

9. The method for providing and using a convenience kit for sterilizing and communicating a desired, selectively determined volume of liquid medication into each of a predetermined number of vessels, according to claim 1, wherein the vessels providing step comprises providing a plurality of capped eye drop bottles and associated filling straws, each such eye drop bottle being made from a converted conventional syringe comprising a valved plunger piston comprising a one-way valve disposed in a barrel of the converted conventional syringe and an eye drop forming adapter being affixed to a standard outlet fitting of the conventional syringe to convert the conventional syringe device to an eye drop bottle device, the barrel, of the syringe, being formed of low density plastic to be compatible with eye drop generation by squeezing the barrel, said valved plunger piston being displaced to be resident within a displaceable portion of an associated eye drop bottle, each of said valved plunger pistons further comprising a straw fitting which communicates with the "open" side of the plunger one-way valve such that fluid flowing from a filling straw affixed to a filling straw fitting permissively flows through the piston valve and further comprises an assembly step of affixing a filling straw to an inherent manifold fitting and to a one-way valve straw fitting while disposing the associated plunger piston at the far end of the syringe of each so affixed syringe away from the inherent manifold fitting before said sterilizing step.

10. The method for providing and using a convenience kit for sterilizing and communicating a desired, selectively determined volume of liquid medication into each of a predetermined number of vessels, according to claim 9, further comprising the following steps for using a sterilized convenience kit made according to the present invention:
   a. provide the container filled with an appropriate volume of prepared liquid medication and affix the container to said first sterilizing filter;
   b. with a single continuous act, dispense the liquid medication through the first sterilizing filter thereby purging gas from the pathway and dispensing liquid medication through the pathway and straws into each syringe via an associated piston valve which displaces each associated syringe barrel as the liquid medication is delivered therein and continues barrel filling until the stop retards further filling;
   c. after all syringes are so filled, provide a syringe piston rod for each syringe and, when each syringe is detached from a straw, affix the syringe piston rod to the straw fitting for conventional syringe operation of dispensing the liquid medication kept at the predetermined medical preparation SAL until the cap is removed.

11. The method for providing and using a convenience kit for sterilizing and communicating a desired, selectively determined volume of liquid medication into each of a predetermined number of vessels according to claim 1, wherein said vessels providing step comprises providing silicon free syringes and said medical preparation is Avastin medication which is to be communicated into said silicon free syringes in predetermined selected volumes, comprising the following additional steps:
   a. providing a plurality of needleless connectors and affix one needleless connector to an inherent manifold fitting where a silicone free syringe is to be attached for receiving communicated Avastin medication;
   b. affixing each such syringe to a needleless connector affixed to an inherent manifold fitting site prior to sterilizing said kit to thereby provide a closed pathway from said first medical grade filter through said pathway and through each said needleless connector to communicate Avastin each syringe in an Avastin prepared convenience kit before the sterilizing step;
   c. in preparation for using the sterilized convenience kit with silicone free syringes for Avastin, providing an Avastin medicine filling case and filling stops which are selectively affixed to predetermined sites within said case prior to said medical liquid preparation communicating step to predetermine volume of Avastin medication filling volume to be displaced into each syringe within said case prior to a liquid medical preparation communicating step to predetermine volume of Avastin medication filling volume to be displaced into each syringe;

d. displacing the Avastin prepared convenience kit into said Avastin medicine filling case and affixing said filling stops to selectively determine fill volume of each syringe;

e. performing a liquid displacing step from the container into the manifold, as a single step, communicating the predetermined volume of the sterilized medical preparation into each vessel; and f. removing and capping, with a cap or capping needle, each Avastin filled syringe, one at a time, whereby each associated needleless connector from which the Avastin filled syringe was separated closes the pathway for that syringe to maintain sterility of remaining filled syringes.

12. The method for providing and using a convenience kit for sterilizing and communicating a desired, selectively determined volume of liquid medication into each of a predetermined number of vessels according to claim 1, wherein said manifold providing step comprises a step of providing a plurality of manifolds sequentially linked and disposed in an optional configuration comprising being stacking and aligned linearly such that more vessels can be filled via the first medical grade sterilizing filter than by using a single manifold.

13. The method for providing and using a convenience kit for sterilizing and communicating a desired, selectively determined volume of liquid medication into each of a predetermined number of vessels, according to claim 1, wherein the vessels providing step comprises providing a predetermined number of eye drop bottles modified according to the present invention.

* * * * *